United States Patent [19]

Waterfield

[11] Patent Number: 5,258,173
[45] Date of Patent: Nov. 2, 1993

[54] DENTRIFICE COMPOSITIONS

[75] Inventor: Philip C. Waterfield, New Brighton Wirral, Great Britain

[73] Assignee: Chesebrough-Pond's USA Co., Division of Conopco, Inc., Greenwich, Conn.

[21] Appl. No.: 883,073

[22] Filed: May 15, 1992

[30] Foreign Application Priority Data

May 17, 1991 [GB] United Kingdom ............... 9110721

[51] Int. Cl.$^5$ ........................... A61K 7/16; A61K 7/18
[52] U.S. Cl. ....................................... 424/49; 424/52; 424/650
[58] Field of Search .................... 424/49-58, 424/650

[56] References Cited

U.S. PATENT DOCUMENTS

| | | | |
|---|---|---|---|
| 3,887,701 | 6/1975 | Nachtigal | 424/52 |
| 3,925,543 | 12/1975 | Donohue | 424/52 |
| 3,992,519 | 11/1976 | Hoffmann et al. | 424/52 |
| 4,364,794 | 12/1982 | Ochiai et al. | . |
| 4,411,885 | 10/1983 | Barels et al. | 424/52 |
| 5,094,841 | 3/1992 | Fine | 424/52 |
| 5,094,842 | 3/1992 | Riley | 424/52 |
| 5,096,702 | 3/1992 | Rolla et al. | 424/52 |

FOREIGN PATENT DOCUMENTS

| | | |
|---|---|---|
| 1295306 | 5/1962 | France . |
| 2406437 | 5/1979 | France . |
| 60-075418 | 4/1985 | Japan . |
| 63-066113 | 3/1988 | Japan . |
| 804486 | 11/1958 | United Kingdom . |
| 809513 | 2/1959 | United Kingdom . |
| 845611 | 8/1960 | United Kingdom . |
| 922385 | 3/1963 | United Kingdom . |

OTHER PUBLICATIONS

Patent Abstracts of Japan–vol. 8, No. 56, Mar. 14, 1984 and JP-A-58 213 706 (RAION) Dec. 12, 1983.
Patent Abstracts of Japan–vol. 11, No. 398, Dec. 25, 1987 and JP-A-62 161 715 (KAO Corporation) Jul. 17, 1987.
Patent Abstracts of Japan–vol. 9, No. 180, Jul. 25, 1985 and JP-A-60 048 920 (Ajinomoto) Mar. 16, 1985.

Primary Examiner—Shep K. Rose
Attorney, Agent, or Firm—Milton L. Honig

[57] ABSTRACT

The present invention relates to a dentifrice composition comprising a stannous compound that releases stannous ions in the composition such as stannous fluoride or stannous pyrophosphate. These stannous ions can be converted in the composition into the inactive stannic ions, and to prevent such conversion according to the present invention an antioxidant is incorporated into the composition, such as butylated hydroxyanisole, butylated hydroxytoluene and ethyl vanillin.

3 Claims, 1 Drawing Sheet

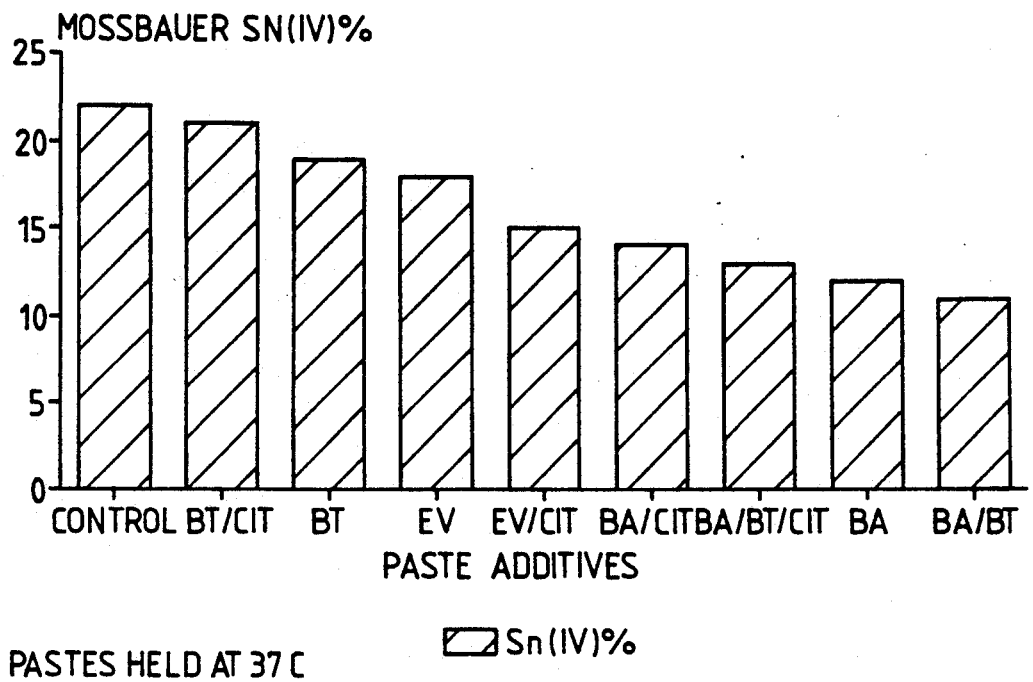
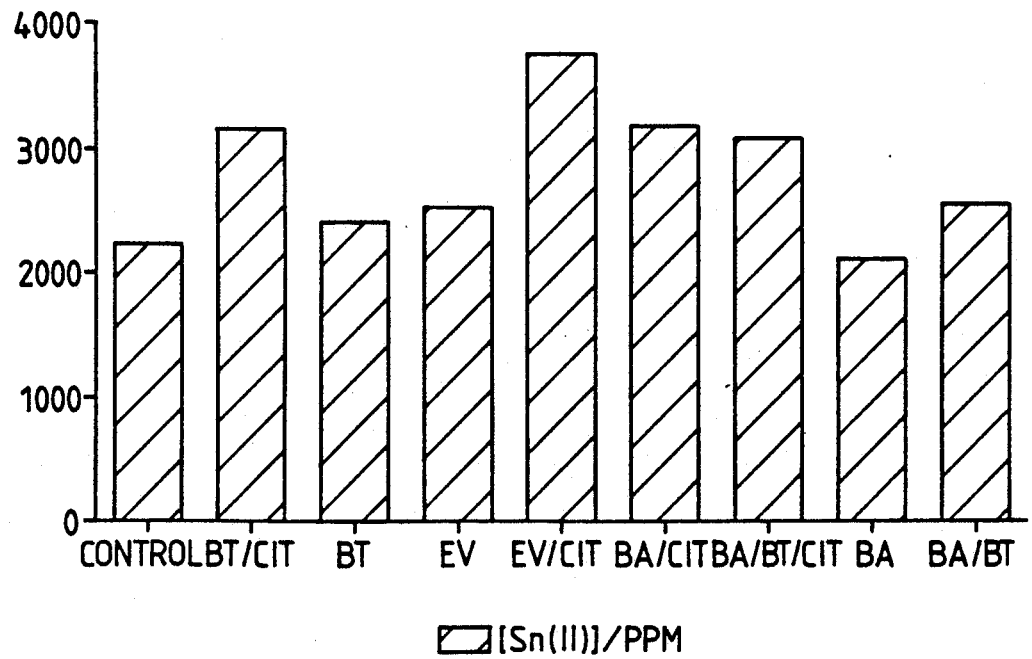

DENTRIFICE COMPOSITIONS

BACKGROUND OF THE INVENTION

1. Field of the Invention

The present invention relates to dentifrice compositions containing stannous compounds.

2. Related Art

There have been many proposals in the prior art to incorporate stannous compounds into oral health care products for the purpose of achieving particular clinical benefits such as caries prevention, plaque control or the reduction of gingivitis. These stannous compounds are compounds which, upon association with water, are capable of yielding stannous ions, as it is actually the stannous ion which is active against oral bacteria.

However, the incorporation of stannous compounds into dentifrice compositions presents problems in that the stannous ions tend to react with other components of the dentifrice composition to form insoluble stannous compounds, which reduces the effective amount of stannous ions in the composition and thus renders the stannous compound less efficacious. In addition, the active stannous ion is particularly prone to oxidation, e.g. by air or an oxidizing agent, the stannous ion being converted thereby into the inactive stannic form.

In GB-A-804,486 it is proposed to overcome the problem that stannous ions react with other components of a dentifrice composition by using a slightly soluble stannous compound e.g. stannous pyrophosphate, thus maintaining a "reservoir" of stannous tin in the form of an undissociated stannous compound which replenishes stannous ions that have reacted with other components of the dentifrice composition.

We have found, however, that the inclusion of such slightly soluble stannous compounds, e.g. stannous pyrophosphate, still gives rise to the formation of inactive stannic compounds.

According to the present invention it has now been found that the conversion of stannous ions in a dentifrice composition into inactive stannic ions can be significantly reduced or prevented by the inclusion in the dentifrice composition of an antioxidant which is a radical inhibitor. Since dentifrice compositions do not normally contain an oxidizing agent and are usually packed in a closed container, it was quite unexpected that the use of an antioxidant of the radical inhibitor type did significantly reduce and prevent the conversion of stannous ions into stannic ions in such a dentifrice composition.

SUMMARY OF THE INVENTION

Consequently, in its broadest aspect, the present invention embraces a dentifrice composition which comprises an effective amount of a stannous compound capable of yielding stannous ions upon association with water, and an effective amount of an antioxidant which is a radical inhibitor capable of reducing or preventing the conversion of the stannous ions in the dentifrice composition into stannic ions.

BRIEF DESCRIPTION OF THE DRAWINGS

The features and advantages of the present invention will more fully be appreciated by reference to the drawing in which:

FIG. 1 is a graph depicting the oxidative stability of stannous ions in pastes containing antioxidants; and FIG. 2 is a graph depicting the soluble stannous stability in pastes containing antioxidants.

DETAILED DESCRIPTION

The stannous compounds which are suitable for inclusion in dentifrice compositions are known per se. Typical examples of suitable stannous compounds are stannous compounds with inorganic or organic counterions. It can be a highly soluble stannous salt, or it can be a sparingly soluble stannous salt. Highly soluble stannous salts are e.g. stannous fluoride, stannous chloride, stannous acetate, sodium stannous fluoride, potassium stannous fluoride, stannous hexafluorozirconate, stannous sulphate, stannous tartrate, stannous gluconate, etc. Of these highly soluble stannous salts, stannous fluoride is the preferred stannous salt.

Sparingly soluble stannous salts are e.g. stannous pyrophosphate, stannous metaphosphate, stannous oxalate, stannous phosphate, etc. Stannous pyrophosphate is a preferred sparingly soluble stannous salt. Mixtures of various highly soluble stannous salts may also be used, as well as mixtures of various sparingly soluble stannous salts and mixtures of highly and sparingly soluble stannous salts. A preferred mixture is the mixture of stannous fluoride and stannous pyrophosphate.

In general, the stannous salt is used in such an amount in the oral composition that there is an effective amount of active dissolved stannous ions available in the composition to achieve an anti-caries, antigingivitis or antiplaque efficacy. For the highly soluble stannous salts, this amount will generally range from 0.01–10%, preferably from 0.02–5%, and particularly preferably from 0.1–3% by weight of the oral composition. As regards the sparingly soluble stannous salts, these ranges are 0.05–10%, preferably 0.1–5%, and particularly preferably 0.1–3% by weight of the oral composition.

Antioxidants which are radical inhibitors are known per se. Both synthetically made or naturally occurring antioxidants are suitable in the present invention. Typical examples of suitable antioxidants in the present invention are propyl gallate, butylated hydroxyanisole (BHA), butylated hydroxytoluene (BHT), ethyl vanillin, rosemary oil, lecithin, vitamin E, rutin, morin, fisetin and other bioflavonoids. Mixtures of various antioxidants can also be used.

The antioxidant is used in an effective amount to significantly reduce or prevent the conversion of stannous ions into stannic ions. In general, low amounts of the antioxidants are already sufficient. Thus, the amount may range from 0.001–2%, usually from 0.015–1.5%, and preferably from 0.02–1% by weight of the dentifrice composition. Naturally, within the above framework the type of antioxidant and the level thereof will also be governed by ecological and safety approval factors.

Preferred antioxidants are BHA, BHT, and ethyl vanillin.

The oral composition of the present invention may contain an orally acceptable medium which contains usual additional ingredients in conventional amounts, depending upon the final form of the composition, i.e. a dentifrice, a mouthwash, a gel and the like. Thus, as a dentifrice it will usually comprise an abrasive cleaning agent in an amount of from 3–75 % by weight. Suitable abrasive cleaning agents are milled or unmilled particulate aluminas; silica xerogels, hydrogels and aerogels and precipitated particulate silicas; calcium pyrophosphate; insoluble sodium metaphosphate; calcium carbonate; dicalcium orthophosphate; particulate hydroxyapatite and so on.

Furthermore, the dentifrice may contain a liquid phase comprising water and a humectant in various relative amounts, in an amount of 10-99% by weight. Typical humectants are glycerol, sorbitol, polyethylene glycol, polypropylene glycol, propylene glycol, hydrogenated partially hydrolyzed polysaccharides and so on.

Binders or thickening agents such as sodium carboxymethyl cellulose, hydroxyethyl cellulose, hydroxypropyl cellulose, xanthan gums, Irish moss, gum tragacanth, finely divided silicas and hectorites may also be included in the dentifrice in an amount of 0.5-10% by weight.

Another conventional ingredient in a dentifrice is an organic surfactant such as soap, an anionic, nonionic, cationic, ampholytic and/or a zwitterionic synthetic surfactant in an amount of 0.2-5% by weight.

When the composition is in the form of a mouthwash, it will usually contain an alcohol, a solubilizer and no abrasive cleaning agent and when in the form of a gel, it will usually contain a thickening agent. Various other optional ingredients may be included in the compositions of the invention, such as flavouring agents, sweetening agents such as sodium saccharinate, whitening agents such as titanium dioxide or zinc oxide, preservatives, vitamins such as vitamin C and E, other antiplaque agents such as zinc salts, e.g. zinc citrate, copper salts, sanguinarine, allantoin, p-aminobenzoic acid derivatives, hexetidine, chlorhexidine, 3-(4-propylheptyl)-4-(2-hydroxyethyl) - morpholine, anti-bacterial agents such as Triclosan (2′,4,4′-trichloro-2-hydroxy-diphenyl ether), anticalculus agents such as di- and/or tetra-alkali metal pyrophosphates, pH-adjusting agents, colouring agents, anti-caries agents such as casein, casein digests, urea, calcium glycerophosphates, sodium trimetaphosphate, sodium fluoride and monosodium fluorophosphate, anti-staining compounds such as silicone polymers, anti-inflammatory agents such as substituted salicylanilides, plant extracts, desensitizing agents for sensitive teeth such as potassium nitrate and potassium citrate, polymers such as polyvinyl methyl ether-maleic anhydride co-polymers and so on.

The present invention will now be further illustrated by the following Examples.

EXAMPLE 1

Five aqueous solutions of stannous fluoride, sodium lauryl sulphate and propyl gallate were prepared. The levels are listed below:

| Solution | SnF2 | SLS | Propyl Gallate |
|---|---|---|---|
| 1 | 0.5% | 1.5% | 0% (Control) |
| 2 | 0.5% | 1.5% | 0.25% |
| 3 | 0.5% | 1.5% | 0.5% |
| 4 | 0.5% | 1.5% | 0.75% |
| 5 | 0.5% | 1.5% | 1.00% |

*All quantities are % w/v.

The solutions were made up in distilled water that had been purged with dry nitrogen gas for 1 hour prior to use. The SLS was added to solubilize the propyl gallate.

The solutions were left at 20° C. for 5 days. After this period, the solutions contained varying amounts of a white precipitate. Small aliquots of the whole solution were taken and analyzed, using Mossbauer Spectroscopy. After 10 days, solutions 1 and 5 were analyzed by Mossbauer Spectroscopy again.

In addition to Mossbauer Spectroscopy, the solutions were analyzed after 5 days for soluble stannous content by polarography. However, unlike the samples taken for Mossbauer analysis, the samples for polarographic analysis were centrifuged first (3000 rpm, 30 minutes) to remove the flocculent white precipitate.

| | Polarographic Analysis: | |
|---|---|---|
| Solution | Soluble Stannous Levels/ppm | |
| 1 | 905 | |
| 2 | 1271 | |
| 3 | 1691 | |
| 4 | 1786 | |
| 5 | 1861 | |

| | Mossbauer Analysis: | | |
|---|---|---|---|
| | Sn (II) | Sn (IV) | Area of Sn (IV) |
| Solution | I.S. | Q.S. | I.S. | Peak % |
| 5 DAYS | | | | |
| 1 | 3.15 | 1.88 | −0.32 | 35 |
| 2 | 3.16 | 1.79 | −0.52 | 6 |
| 3 | 3.16 | 1.80 | −0.57 | 4 |
| 4 | 3.19 | 1.77 | −0.53 | 4 |
| 5 | 3.14 | 1.98 | −0.58 | 5 |
| 10 DAYS | | | | |
| 1 | 3.11 | 1.98 | −0.32 | 54 |
| 5 | 3.14 | 1.80 | −0.57 | 6 |

*All figures given in mmsec-1
*Mossbauer errors +/− 0.05 mmsec-1
*I.S. = Isomer Shift; Q.S. = Quadrupole Split.

It is clear from the polarographic analysis that increasing levels of propyl gallate inhibited the loss of soluble stannous from solution. The polarograph, however, only tests the stannous components in solution. The Mossbauer spectra showed that with no propyl gallate present (solution 1), at least 34 of the total tin was Sn(IV) after 5 days and 54% Sn(IV) at 10 days. Even with only 0.25% of propyl gallate, after 5 days, there was only approximately 6% of Sn(IV) and this level of Sn(IV) contamination was present in the starting materials anyway.

These data showed that the propyl gallate was inhibiting the oxidation of Sn(II) to Sn(IV).

EXAMPLE 2

A series of 6 toothpastes have been formulated, containing different antioxidants. The formulations are listed below. The pastes were stored at 50° C. for 1.7 monts and analyzed, using Mossbauer Spectroscopy.

| Paste | 1 | 2 | 3 | 4 | 5 | 6 |
|---|---|---|---|---|---|---|
| Silica xerogel | 14.67 | 14.67 | 14.67 | 14.67 | 14.67 | 14.67 |
| Silica aerogel | 9.43 | 9.43 | 9.43 | 9.43 | 9.43 | 9.43 |
| Sorbitol (70%) | 46.98 | 46.98 | 46.98 | 46.98 | 46.98 | 46.98 |
| Polyethylene glycol (MW 1500) | 5.24 | 5.24 | 5.24 | 5.24 | 5.24 | 5.24 |
| Xanthan gum | 0.63 | 0.63 | 0.63 | 0.63 | 0.63 | 0.63 |
| Saccharin | 0.24 | 0.24 | 0.24 | 0.24 | 0.24 | 0.24 |
| Sodium fluoride | 0.34 | 0.34 | 0.34 | 0.34 | 0.34 | 0.34 |
| Benzoic acid | 0.1965 | 0.1965 | 0.1965 | 0.1965 | 0.1965 | 0.1965 |
| Titanium dioxide | 1.04 | 1.04 | 1.04 | 1.04 | 1.04 | 1.04 |
| Sodium lauryl sulphate | 1.5 | 1.5 | 1.5 | 1.5 | 1.5 | 1.5 |
| Stannous | 1.0 | 1.0 | 1.0 | 1.0 | 1.0 | 1.0 |

| | -continued | | | | | |
|---|---|---|---|---|---|---|
| pyrophosphate | | | | | | |
| Zinc citrate | 0.5 | 0.5 | 0.5 | 0.5 | 0.5 | 0.5 |
| Flavour | 1.0 | 1.0 | 1.0 | 1.0 | 1.0 | 1.0 |
| Special progallin | 0.05 | — | — | — | — | — |
| Propyl | — | 0.05 | — | — | — | — |

| gallate | | | | | | |
|---|---|---|---|---|---|---|
| BHA | — | — | 0.07 | — | — | — |
| Rosemary oil extract | — | — | — | 1.00 | — | — |
| Ethyl vanillin | — | — | — | — | 1.00 | — |
| BHT | — | — | — | — | — | 0.03 |
| Water | 17.24 | 17.24 | 17.23 | 17.14 | 17.14 | 17.24 |
| Total | 100.00 | 100.00 | 100.00 | 100.00 | 100.00 | 100.00 |

Results:

| Antioxidant in Paste | Sn (II) I.S. | Sn (II) Q.S. | Sn (IV) I.S. | Area of Sn (IV) Peak % |
|---|---|---|---|---|
| Progallin (0.05%) | 2.95 / 3.14 | 2.13 / 1.75 | −0.15 | 5 |
| Propyl Gallate (0.05%) | 2.93 / 3.17 | 2.11 / 1.81 | −0.18 | 6 |
| Butylated Hydroxyanisole (0.07%) | 2.94 / 3.14 | 2.10 / 1.77 | −0.24 | 3 |
| Rosemary Oil Extract | 2.95 / 3.14 | 2.09 / 1.77 | −0.21 | 4 |
| Ethyl Vanillin (1%) | 2.94 / 3.15 | 2.09 / 1.79 | −0.19 | 6 |
| Butylated HydroxyToluene (0.03%) | 2.94 / 3.15 | 2.10 / 1.78 | −0.22 | 4 |

Again, these data showed that the antioxidants inhibited the oxidation of Sn(II) to Sn(IV).

EXAMPLE 3

A series of nine toothpastes having the following formulations were stored for nine months at 37° C, and the amount of Sn (IV) was determined using Mossbauer spectroscopy. The amount of soluble Sn (II) was determined by polarographic analysis. Figures I and II show the results.

These results show, that the inclusion of antioxidants have a beneficial effect on the stability of Sn (II), even in the presence of an additional 0.5% citrate, of which it is known that it can exert a solubilizing effect on stannous ions in certain formulations.

| Paste | Control | BT/CIT | BT | EV | EV/CIT | BA/CIT | BA/BT/CIT | BA | BA/BT |
|---|---|---|---|---|---|---|---|---|---|
| Silica xerogel | 10.00 | 10.00 | 10.00 | 10.00 | 10.00 | 10.00 | 10.00 | 10.00 | 10.00 |
| Silica aerogel | 9.00 | 9.00 | 9.00 | 9.00 | 9.00 | 9.00 | 9.00 | 9.00 | 9.00 |
| Sorbitol (70%) | 45.00 | 45.00 | 45.00 | 45.00 | 45.00 | 45.00 | 45.00 | 45.00 | 45.00 |
| Polyethyleneglycol (MW 1,500) | 5.00 | 5.00 | 5.00 | 5.00 | 5.00 | 5.00 | 5.00 | 5.00 | 5.00 |
| Xanthan gum | 1.20 | 1.20 | 1.20 | 1.20 | 1.20 | 1.20 | 1.20 | 1.20 | 1.20 |
| Titanium doxide | 1.00 | 1.00 | 1.00 | 1.00 | 1.00 | 1.00 | 1.00 | 1.00 | 1.00 |
| Saccharin | 0.13 | 0.13 | 0.13 | 0.13 | 0.13 | 0.13 | 0.13 | 0.13 | 0.13 |
| Sodium fluoride | 0.25 | 0.25 | 0.25 | 0.25 | 0.25 | 0.25 | 0.25 | 0.25 | 0.25 |
| Sodium laurylsulphate | 1.50 | 1.50 | 1.50 | 1.50 | 1.50 | 1.50 | 1.50 | 1.50 | 1.50 |
| Stannous pyrophosphate | 1.00 | 1.00 | 1.00 | 1.00 | 1.00 | 1.00 | 1.00 | 1.00 | 1.00 |
| Zinc citrate | 0.50 | 0.50 | 0.50 | 0.50 | 0.50 | 0.50 | 0.50 | 0.50 | 0.50 |
| Flavour | 1.00 | 1.00 | 1.00 | 1.00 | 1.00 | 1.00 | 1.00 | 1.00 | 1.00 |
| BHA | — | — | — | — | — | 0.07 | 0.07 | 0.07 | 0.07 |
| BHT | — | 0.03 | 0.03 | — | — | — | 0.03 | — | 0.03 |
| Ethyl vanillin | — | — | — | 0.80 | 0.80 | — | — | — | — |
| Sodium citrate | — | 0.325 | — | — | 0.325 | 0.325 | 0.325 | — | — |
| Citric acid | — | 0.175 | — | — | 0.175 | 0.175 | 0.175 | — | — |
| Water | 24.42 | 23.890 | 24.39 | 23.62 | 23.120 | 23.850 | 23.820 | 24.35 | 24.32 |

I claim:

1. A method for inhibiting conversion of stannous ions into inactive stannic ions within a toothpaste composition comprising stabilizing said stannous ions with an antioxidant which is a radical inhibitor, said toothpaste composition consisting essentially of:
   (i) from 10 to 99% by weight of a liquid phase formed of a material selected from the group consisting of water, humectants and combinations thereof;
   (ii) from 0 to 75% by weight of an abrasive cleaning agent;
   (iii) from 0.01 to 10% by weight of a stannous compound capable of yielding said stannous ions upon association with water, said stannous compounds being selected from the group consisting of stannous chloride, stannous acetate, stannous hexafluorozirconate, stannous sulphate, stannous tartrate, stannous gluconate, stannous pyrophosphate, stannous metaphosphate, stannous oxalate, stannous phosphate and combinations thereof; and
   (iv) from 0.001 to 2% by weight of an antioxidant selected from the group consisting of propyl gallate, butylated hydroxyanisole, butylated hydroxytoluene, ethyl vanillin, rosemary oil, lecithin, vitamin E, rutin, morin fisetin and mixtures thereof.

2. A method according to claim 1, wherein said antioxidant is selected from the group consisting of butylated hydroxyanisole, butylated hydroxytoluene and ethyl vanillin.

3. A method according to claim 1 wherein said stannous compound is stannous pyrophosphate.

* * * * *